United States Patent [19]

Curtze

[11] Patent Number: 4,933,449
[45] Date of Patent: Jun. 12, 1990

[54] PREPARING 3-(4 CHLOROPHENYL)-3-(3,4-DIMETHOXYPHENYL) ACRYLIC ACID MORPHOLIDE IN THE PRESENCE OF POTASSIUM TERT-BUTYLATE

[75] Inventor: Jürgen Curtze, Johannisberg, Fed. Rep. of Germany

[73] Assignee: Shell Internationale Research Maatschappij B.V., The Hague, Netherlands

[21] Appl. No.: 200,856

[22] Filed: Jun. 1, 1988

[30] Foreign Application Priority Data

Jun. 11, 1987 [DE] Fed. Rep. of Germany ....... 3719488

[51] Int. Cl.⁵ ................. C07D 295/18; C07C 103/20; C07C 103/22; C07C 103/133
[52] U.S. Cl. .................................... 544/174; 544/176; 564/204; 564/205
[58] Field of Search ................ 564/204, 205; 544/176, 544/174

[56] References Cited

FOREIGN PATENT DOCUMENTS 0219756 4/1987 European Pat. Off. ............ 564/204

OTHER PUBLICATIONS

Theilheimer, Synthetic Methods of Organic Chemistry, vol. 19, p. 314, #749 (1965).
Chodkiewicz, W. et al., Bull. Soc. Chim. France, 1958, 1586–91.
Drake, N. L. et al., J. Amer. Chem. Soc., 70, 677–680 (Feb. 1948).

Primary Examiner—Floyd D. Higel

[57] ABSTRACT

The invention provides a process for the preparation of 3,3-diaryl acrylic acid amides of the formula

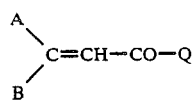 (I)

in which A, B and Q are as defined in the specification, characterized by condensing a compound of formula

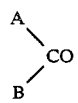 (II)

with a compound of formula

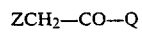 (III)

in which Z represents a hydrogen or halogen atom, and, if an intermediate compound is formed of formula

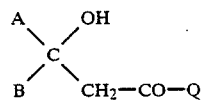 (IV)

dehydrating the intermediate compound.

3 Claims, No Drawings

PREPARING 3-(4 CHLOROPHENYL)-3-(3,4-DIMETHOXYPHENYL) ACRYLIC ACID MORPHOLIDE IN THE PRESENCE OF POTASSIUM TERT-BUTYLATE

The invention concerns a new process for the preparation of 3,3-diaryl acrylic acid amides of the formula

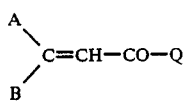  (I)

in which
A represents

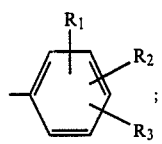

B represents

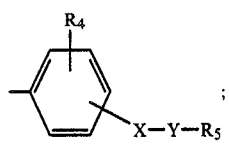

and
Q represents

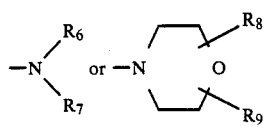

where
$R_1$ represents a $C_{1-4}$ alkyl, $C_{1-4}$ alkoxy, amino, mono- or di-($C_{1-4}$ alkyl)amino, $C_{3-4}$ alkenyl, $C_{3-4}$ alkynyl, $C_{3-4}$ alkenyloxy, $C_{3-4}$ alkynyloxy or $C_{3-6}$ cycloalkyl group;
$R_2$ represents a $C_{1-4}$ alkyl or $C_{1-4}$ alkoxy group or a halogen atom;
$R_3$ represents a hydrogen or halogen atom;
$R_4$ represents a hydrogen or halogen atom or a $C_{1-4}$ alkyl or $C_{1-4}$ alkoxy group;
$R_5$ represents a hydrogen atom, a phenyl group optionally substituted by one or more substituents selected from $C_{1-4}$ alkyl, $C_{1-4}$ alkoxy, halogen, phenyl and phenoxy moieties, a $C_{1-12}$ alkyl group optionally substituted by one or more halogen atoms, a $C_{3-7}$ cycloalkyl group, a $C_{2-6}$ alkenyl or a $C_{2-6}$ alkynyl group each optionally substituted by a phenyl group, or a naphthyl or $C_{5-8}$ cycloalkenyl group;
—X—Y— represents a single bond or a —O—, —S-(O)$_p$— where p is 0, 1 or 2, —N=N—, —CHR$_{10}$—O—, —O—CHR$_{10}$—, —CHR$_{10}$—S(O)$_p$—, —S-(O)$_p$—CHR$_{10}$—, —C$_n$H$_{2n}$— where n is an integer from 1 to 10, —HC=CH— or —C≡C— moiety;
$R_6$ represents a $C_{1-4}$ alkyl, $C_{3-7}$ cycloalkyl, benzyl, $C_{3-4}$ alkenyl or $C_{3-4}$ alkynyl group;
$R_7$ represents a $C_{1-4}$ alkyl group;
$R_8$ represents a hydrogen atom or a $C_{1-4}$ alkyl or $C_{1-4}$ alkoxy group; and
$R_9$ and $R_{10}$ independently represent a hydrogen atom or a $C_{1-4}$ alkyl group.

Compounds of formula I are fungicidally active and are particularly useful in the control of phytopathogenic fungi, especially Plasmopara viticola and Phytophthora infestans. Particularly preferred compounds of formula I in this respect are those in which A represents a 3,4-dimethoxyphenyl, 3-ethoxy-4-methoxyphenyl, 3-chloro-4-methoxyphenyl, 3-bromo-4-methoxyphenyl, 3-methyl-4-methoxyphenyl, 3-ethyl-4-methoxyphenyl, 3-propyl-4-methoxyphenyl, 3,4-dimethylphenyl, 3-amino-4-methoxyphenyl, 3,5-dichloro-4-aminophenyl or 3-methoxy-4-methylphenyl group and, of these, 3,4-dimethoxyphenyl is especially preferred. It is also preferred that Q represents a morpholino group. An especially preferred compound of formula I is 3-(4-chlorophenyl)-3-(3,4-dimethoxyphenyl) acrylic acid morpholide.

Compounds of formula I form the subject of European patent applications nos. 84102012.6 and 86113835.2, published as EP No. 0 120 321 A1 and EP No. 0219756 A1 respectively, and these documents describe the only methods previously disclosed for the preparation of these compounds. However, it has now been surprisingly discovered that compounds of formula I can also be prepared by reacting a benzophenone with an appropriate acetamide, in a modification of a known reaction, followed, if necessary, by dehydration.

According to the present invention there is therefore provided a process for the preparation of a compound of formula I, as defined above, characterised by condensing a compound of formula

  (II)

in which A and B have the meanings given above, with a compound of formula

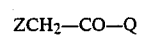  (III)

in which Z represents a hydrogen or halogen, especially a chlorine or bromine, atom and Q has the meaning given above, and, if an intermediate compound is formed of formula

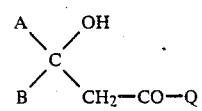  (IV)

in which A, B and Q have the meanings given above, dehydrating the intermediate compound.

The above process can be represented by the following reaction scheme:

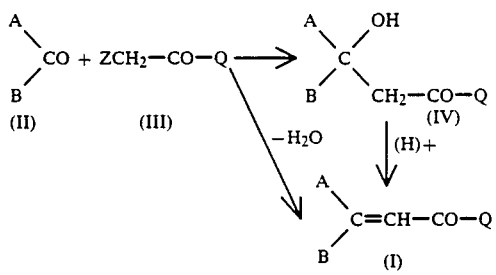

In this scheme A, B, Q and Z are as defined above. As shown in the scheme, depending on the reaction conditions and reagents used, the above reaction may proceed directly to the final product of formula I in one step or may proceed in two steps via an intermediate of formula IV. In the latter case, a separate dehydration step is required to produce the final product of formula I.

In the case where Z represents a hydrogen atom, the condensation reaction may be carried out in the presence of a strong base. Suitable strong bases include alkali hydroxides, alkali carbonates, potassium tert-butylate and tert-butyl lithium. Depending on the base used and the temperature at which the reaction is carried out, compounds of formula I are sometimes formed directly by elimination of water without the need for a separate dehydration step. (cf. W. Chodkiewicz et al., Bull. Soc. Chim. France, 1958, 1586-9).

In the case where Z represents a halogen, especially a bromine, atom, the condensation reaction is suitably carried out in the presence of zinc (cf. N.L. Drake et al., J. Am. Chem. Soc., 70, 677 (1948)). In this case, the reaction usually proceeds via an isolatable intermediate of formula IV thus requiring a separate dehydration step.

The reactions may be carried out in the presence of an inert solvent, such as toluene, benzene, diethyl ether, diisopropyl ether, diglyme, tetrahydrofuran, dimethyl formamide, acetone or ethylene chloride. Alternatively, an excess of one of the reactants may also serve as a solvent. Depending on the reactivity of the reactants, the condensation reaction may be carried out at any temperature from room temperature to the reflux temperature of the reaction mixture.

If a compound of formula IV is formed as an intermediate product, dehydration can be started by heating the compound in an inert solvent, such as toluene, benzene, etc, optionally, in the presence of an acid such as toluene sulphonic acid, sulphuric acid, phosphoric acid and hydrochloric acid. Alternatively, dehydration may be accomplished simply by reaction with an appropriate acid, such as those listed above. Many acids, such as glacial acetic acid, are useful principally as a solvent. However, some acids, such as formic acid, have both acid and solvent functions.

Compounds of formula II and formula III are either known compounds or can be produced from known compounds by known methods.

The process of the invention is illustrated by the following specific examples.

COMPARATIVE EXAMPLE 1

Preparation of 3-(4-chlorophenyl)-3-(3,4-dimethoxyphenyl)acrylic acid morpholide 6.92 g (25 mmol) 4-chloro-3',4'-dimethoxybenzophenone, 12.9 g (100 mmol) N-acetylmorpholine and 11.2 g (170 mmol) powdered potassium hydroxide (85%) were mixed well and allowed to stand at room temperature for 30 minutes, with occasional stirring. The viscous mass so obtained was then added to a vigorously stirred mixture of 100 ml water and 50 ml toluene. The toluene phase was dried and separated over a column containing 50 g silica gel using 150 ml each of 95:5, 90:10 and 80:20 toluene-acetone mixture as eluant. The fractions with an Rf value of 0.37 (Toluene/Acetone 7:3) were evaporated in a rotary evaporator, after which 0.8 g of the title compound were obtained by trituration with a little diisopropyl ether.

By evaporating the fractions with an Rf value of 0.52, 3.4 g (33.5% of theory) of 3-(4-chlorophenyl)-3-(3,4-dimethoxyphenyl)-3-hydroxypropionic acid morpholide were obtained, m.pt. 150° C. For the dehydration step, this substance was then dissolved in 10 ml glacial acetic acid by warming, 0.1 ml conc. sulphuric acid were added and the mixture was then boiled under reflux for 5 minutes. After cooling to 50° C., the mixture was stirred into 100 ml water. The oil that initially separated out solidified on further stirring. The substance was then filtered off under suction, washed with water and dried. Thin layer chromatography (TLC) indicated that the final product was substantially pure.

Yield: 2.9 g (30% of theory).
Total yield: 3.7 g (38% of theory), TLC-pure.

EXAMPLE 1

Preparation of 3-(4-chlorophenyl)-3-(3,4-dimethoxyphenyl)acrylic acid morpholide 13.84 g (50 mmol)

4-chloro-3',4'-dimethoxybenzophenone, 7.75 g (60 mmol) N-acetylmorpholine, 7.29 g (65 mmol) potassium tert-butylate and 75 ml anhydrous toluene were mixed and stirred for 2 hours under nitrogen at 80° C. The solution was then cooled, extracted with 100 ml water, dried and evaporated in a rotary evaporator. 11.5 g of a viscous oil were obtained, which were then heated with 50 ml diisopropyl ether whilst stirring. The oil crystallised on cooling and rubbing. The crystals were then filtered off under suction, washed with a little diisopropyl ether and dried.

Yield: 9.25 g (48% of theory).
M.pt: 122-148° C.
TLC-pure, R.f. value: 0.38 in 7:3 toluene/acetone.

EXAMPLE 2

Preparation of 3-(4-chlorophenyl)-3-(3,4-dimethoxyphenyl) acrylic acid morpholide 5.53 g (20 mmol) 4-chloro-3',4'-dimethoxybenzophenone, 3.23 g (25 mmol) N-acetylmorpholine, 3.29 g (50 mmol) powdered potassium hydroxide (85,%) and 30 ml absolute tetrahydrofuran were stirred under reflux for 5 hours under nitrogen. After cooling, the liquid paste so obtained was added to a well stirred mixture of 100 ml water and 50 ml toluene. The toluene phase was dried and separated over a column containing 50 g silica gel, using 100 ml each of 95:5, 90:10 and 80:20 toluene-acetone mixture as eluant. The fractions containing a substance with an Rf-value of 0.38 (Toluene/Acetone 7:3) were then evaporated in a rotary evaporator. The oil thus obtained solidified on trituration with a little diisopropyl ether.

M.pt: 125°–145° C.

Yield: 3.25 g (42% of theory).

I claim:

1. A process for the preparation of a compound of the formula

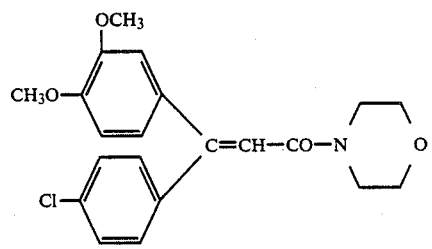

characterized by condensing a compound of formula

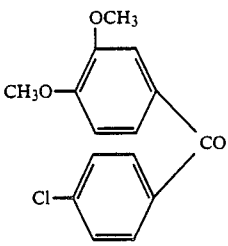

with a compound of formula

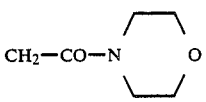

in the presence of potassium tert-butylate.

2. A process according to claim 1 in which the reaction is carried out at a temperature ranging from room temperature to the reflux temperature of the reaction mixture.

3. A process according to claim 1 or 2 in which the reaction is carried out in the presence of a solvent selected from the group consisting of toluene, benzene and diisopropyl ether.

* * * * *